(12) United States Patent
Choi et al.

(10) Patent No.: US 12,306,182 B2
(45) Date of Patent: May 20, 2025

(54) TUBERCULOSIS DIAGNOSIS METHOD AND APPARATUS THEREFOR

(71) Applicant: BODITECH MED INC., Gangwon-Do (KR)

(72) Inventors: Dong Hwan Choi, Gangwon-Do (KR); Kyungjoon Kang, Gangwon-do (KR); Won Hee Lee, Gangwon-do (KR)

(73) Assignee: BODITECH MED INC., Gangwon-Do (KR)

( * ) Notice: Subject to any disclaimer, the term of this patent is extended or adjusted under 35 U.S.C. 154(b) by 1042 days.

(21) Appl. No.: 17/294,072

(22) PCT Filed: Feb. 25, 2019

(86) PCT No.: PCT/KR2019/002292
§ 371 (c)(1),
(2) Date: May 14, 2021

(87) PCT Pub. No.: WO2020/111393
PCT Pub. Date: Jun. 4, 2020

(65) Prior Publication Data
US 2022/0011305 A1    Jan. 13, 2022

(30) Foreign Application Priority Data
Nov. 27, 2018 (KR) .................. 10-2018-0148847

(51) Int. Cl.
*G01N 33/543* (2006.01)
*G01N 33/569* (2006.01)
*G01N 33/68* (2006.01)

(52) U.S. Cl.
CPC . *G01N 33/54386* (2013.01); *G01N 33/54388* (2021.08); *G01N 33/5695* (2013.01); *G01N 33/6866* (2013.01); *G01N 2333/57* (2013.01)

(58) Field of Classification Search
CPC ....... G01N 33/54386; G01N 33/54388; G01N 33/5695; G01N 33/6866; G01N 2333/57
See application file for complete search history.

(56) References Cited

U.S. PATENT DOCUMENTS

| | | | |
|---|---|---|---|
| 5,935,864 A * | 8/1999 | Schramm | A61B 5/150358 422/410 |
| 2009/0088336 A1* | 4/2009 | Burd | G01N 33/5304 506/9 |
| 2017/0087547 A1 | 3/2017 | Laukkonen et al. | |

FOREIGN PATENT DOCUMENTS

| | | |
|---|---|---|
| CN | 107045065 A | 8/2017 |
| CN | 107 894 502 A | 4/2018 |
| CN | 207 541 079 U | 6/2018 |
| JP | 2011515171 A | 5/2011 |
| JP | 2016161540 A | 9/2016 |
| KR | 20090048970 A | 5/2009 |
| KR | 20120061714 A | 6/2012 |
| KR | 1020120061714 A | 6/2012 |
| KR | 101168232 B1 | 7/2012 |
| KR | 101190191 B1 | 10/2012 |
| KR | 20160137007 A | 11/2016 |
| KR | 20170023822 A | 3/2017 |
| WO | 2009064079 A1 | 5/2009 |

OTHER PUBLICATIONS

Saracino, Annalisa et al. "QuantiFERON-TB Gold In-Tube test (QFT-GIT) for the screening of latent tuberculosis in recent immigrants to Italy." The new microbiologica vol. 32,4 (2009): 369-76. (Year: 2009).*
Corstjens, Paul L A M et al. "A user-friendly, highly sensitive assay to detect the IFN-gamma secretion by T cells." Clinical biochemistry vol. 41,6 (2008): 440-4. doi:10.1016/j.clinbiochem.2007.12.015 (Year: 2008).*
Seth, Misago et al., "Immunochromatographic thread-based test platform for diagnosis or infectious disease". Microfluidics and Nanofluidics, vol. 22 article No. 45. https://doi.org/10.1007/s10404-018-2065-1 2018.03.31 (Year: 2018).*
Translation of JP2016161540A (Year: 2016).*
Ferrara, Giovanni et al., Use in routine clinical practice of two commercial blood tests for diagnosis of infection with *Mycobacterium tuberculosis*: a prospective study, The Lancet, Apr. 22, 2006, pp. 1328-1334, vol. 367.
"Sample to Insight Blood Collection and Handling Training Guide QuantiFERON—TB Gold" dated Apr. 1, 2017, 12 pages.
"The Capillary Blood Collection GK with accessories", by Kabe Labortechnik, dated Nov. 9, 2018, 12 pages.
Giovanni Ferrara et al, "Use in routine clinical practice of two commercial blood tests for diagnosis of infection with *Mycobacterium tuberculosis*: a prospective study", www.thelancet.com vol. 367 Apr. 22, 2006, 7 pages.

* cited by examiner

*Primary Examiner* — Gregory S Emch
*Assistant Examiner* — McKenzie A Dunn
(74) *Attorney, Agent, or Firm* — Klintworth & Rozenblat IP LLP (57) ABSTRACT

An apparatus for easily and conveniently diagnosing tuberculosis including a blood collecting device is provided. The blood collecting device comprises a support part including a first surface, a second surface formed opposite to the first surface, and a communication hole through which a solution is movable. The communication hole is formed between the first surface and the second surface. A blood collecting tip is attached to the first surface and has a capillary tube connected to the communication hole. According to the present disclosure, a small amount of peripheral blood is collected using a capillary phenomenon and the collected whole blood is used as it is without separating a blood corpuscle therefrom by centrifugation and the like to diagnose tuberculosis.

5 Claims, 7 Drawing Sheets

TUBERCULOSIS DIAGNOSIS METHOD AND APPARATUS THEREFOR

TECHNICAL FIELD

The present invention generally relates to a method for diagnosing tuberculosis and an apparatus therefor, and more particularly, to a method for collecting blood easily and diagnosing tuberculosis easily using whole blood without separating blood cells and an apparatus therefor.

BACKGROUND ART

Tuberculosis is a chronic disease caused by *Mycobacterium tuberculosis* infection and is one of the most serious infectious diseases such as human immunodeficiency virus (HIV) or malaria in the world. Tuberculosis is categorized into two in a clinical point of view: active tuberculosis and latent tuberculosis. The diagnosis of latent tuberculosis is very important because the tuberculosis of 10% of infected people with reduced immunity grows to be active tuberculosis. Latent tuberculosis infection (LTBI) has no symptoms and does not spread to others because there are only a few *Mycobacterium tuberculosis* bacteria in the body. In addition, it is not possible to directly identify a small number of bacteria remaining in the body since it turns out to be normal both on the Mycobacterial test and on the chest X-ray test. So, the presence of tuberculosis infection is diagnosed through an immunological response to the *Mycobacterium tuberculosis* antigens.

The interferon-gamma releasing assay (IGRA) has been introduced and used worldwide as a method of diagnosing tuberculosis infection. IGRA is a cell-mediated in vitro cell activity measurement method that detects infection by measuring interferon gamma (Interferon-γ, INF-γ) secreted by T-immune cells that specifically react to the *Mycobacterium tuberculosis* antigens. This method will be described in detail. First, in order to react the immune cells and the antigens specific to *Mycobacterium tuberculosis*, the antigens are applied and dried on the wall of a blood collection tube at a specific concentration. And then, after injecting the blood collected through an intravenous injection into the blood collection tube, the dried antigens are eluted by the blood, and the eluted antigens react to immune cells in the blood to cause an in vitro immune response. As a result, INF-γ is secreted by the T cells that react to the antigens. In this way, measuring the INF-γ to determine the presence of latent tuberculosis infection is the principle of a general IGRA assay. In this case, INF-γ is measured using an enzyme linked immunoassay (ELISA) or an ELISA-based assay reagent.

In this case, ELISA is used for the whole blood collected from the patient. While using ELISA, it is difficult to control non-specific reactions caused by blood cells and various substances in the whole blood besides the specific reaction with INF-γ in the plasma of the whole blood. Therefore, the blood collection tube used in IGRA should be a blood collection tube treated with a separating gel that separates blood cells from plasma, and a centrifugation procedure for separating blood cells is essential. In addition, due to the nature of the latent tuberculosis test, it is necessary to collect blood through intravenous injection. In this case, about 1000 μL of blood is required to be collected for diagnosis of tuberculosis. However, this can put a strong psychological and physical burden on children or the elderly. Furthermore, it requires ELISA reagents, measuring equipment, and equipment such as a centrifuge for separating blood cells from venous blood as well as clinical pathologists or nurses who perform a series of the processes. It not only has to go through technically complex processes, but also economically puts a feeling of economic burden on the test subjects due to the expensive test cost. Therefore, it is difficult to manage tuberculosis, such as latent tuberculosis testing, in underdeveloped countries despite their high incidence rates.

DISCLOSURE

Technical Problem

The present invention enables to diagnose tuberculosis simply and quickly using whole blood without separating blood cells by centrifugation or the like after collecting a small amount of peripheral blood other than venous blood.

Technical Solution

In an embodiment of the present invention, a tuberculosis diagnosis apparatus comprises a blood collection device, wherein the blood collection device comprises: a support part consisting of a first surface, a second surface formed on the opposite side of the first surface, and a communication hole in which a solution can move between the first surface and the second surface; and a blood collection tip attached to the first surface and formed with a capillary tube connected to the communication hole.

Preferably, the tuberculosis diagnosis apparatus further comprises: a dilution tube coupled to the first surface and capable of diluting the blood collected on the blood collection tip; a reaction tube having antigens specific to *Mycobacterium tuberculosis* inside a container and coupled to the second surface to receive the solution of the dilution tube so as to react the solution of the dilution tube with the antigens; and a dispensing nozzle coupled to the second surface.

Preferably, the tuberculosis diagnosis apparatus further comprises: besides the blood collection device, a wick with antigens specific to *Mycobacterium tuberculosis* immobilized; a reaction tube coupled to the first surface and for surrounding the blood collection tip; and a buffer tube coupled to the first surface and having a buffer capable to be mixed with the residual blood in the blood collection tip, wherein the residual blood was subjected to immune response.

Furthermore, in another embodiment of the present invention, a tuberculosis diagnosis method comprises the steps of: diluting blood collected by a blood collection tip of a blood collection device of claim 1; reacting diluted solution with antigens specific to *Mycobacterium tuberculosis* in a reaction tube; and dispensing solution of the reaction tube.

Furthermore, in another embodiment of the present invention, a tuberculosis diagnosis method comprises the steps of: inserting a wick to which antigens specific to *Mycobacterium tuberculosis* are immobilized into a blood collection tip of a blood collection device; reacting the antigens specific to *Mycobacterium tuberculosis* with blood in the blood collection tip; contacting the reacted blood in the blood collection tip with the inside of a buffer tube containing a buffer and antibody conjugates specific for interferon gamma; and dispensing a solution of a buffer tube, wherein the solution was contacted with the reacted blood in the blood collection tip.

Advantageous Effects

The present invention as described above enables to collect a small amount of peripheral blood rather than venous blood by using a capillary phenomenon, and to diagnose tuberculosis using the whole blood without separating the blood cells by centrifugation, etc., so that it is possible to diagnose tuberculosis more easily and quickly than the conventional ELISA-based IGRA that uses venous blood.

BEST MODE

Various exemplary embodiments of the invention are fully discussed in detail hereinafter with reference to the accompanying drawings.

Figure 1:
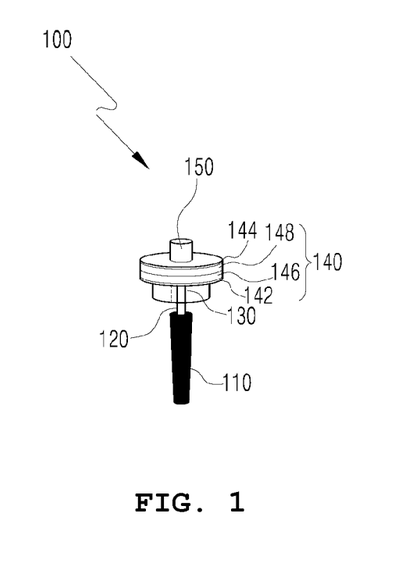
FIG. 1 depicts a main configuration of a blood collection device according to an embodiment of the present invention.
Figure 2A:
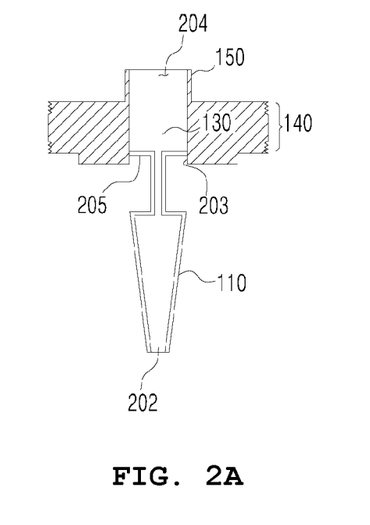
FIG. 2A is a cross section view illustrating a blood collection device according to an embodiment of the present invention, and FIG. 2B. is a longitudinal section view from above illustrating the dispensing nozzle of the blood collection device of the present invention.
Figure 2B:
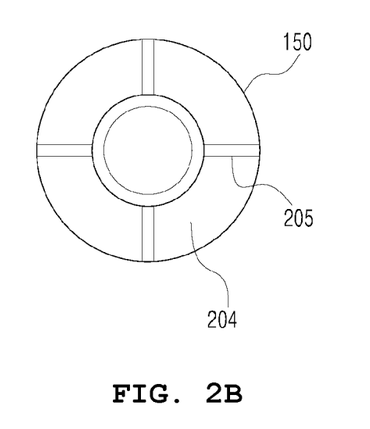

FIG. 1 depicts a main configuration of a blood collection device 100 according to an embodiment of the present invention. FIG. 2A is a cross section view illustrating a blood collection device according to an embodiment of the present invention. From the bottom of the drawing, illustrated are a cross section of the inside 202 of the blood collection tip, the inside 203 of the communication hole 130, the tip fixing part coupling part 205, and the inside 204 of the dispensing nozzle. FIG. 2A is a longitudinal section view from above illustrating the dispensing nozzle of the blood collection device of the present invention. It shows the longitudinal section of the inside 204 of the dispensing nozzle, the tip fixing part coupling part 205 and the dispensing nozzle 150.

Referring to FIG. 1, a blood collection device 100 according to an embodiment of the present invention includes a supporting part 140 and a blood collection tip 110. The support part 140 comprises a first surface 146, a second surface 148 formed on the opposite side from the first side 146, and a communication hole 130 for allowing solution to move between the first side 146 and the second side 148. And, the blood collection tip 110 is attached to the first surface 146 by means of the tip fixing part 120, and the blood collection tip 110 having a capillary tube is connected to the communication hole 130.

The blood collection tip 110 may be formed tapered. It is in order to minimize the amount of blood deposited on the outside of the tip when it is filled with blood, and to make it easier to wipe off external blood. The wider side of the blood collection tip 110 is attached by means of the tip fixing part 120 in the center of the first surface 146 of the support part 140, and blood is collected by means of a capillary tube formed therein. The blood collection tip 110 may be made of a cellulose acetate material having excellent water immersion in order to maximize a capillary phenomenon. And, it is desirable to have a flat structure in order to more easily remove residual blood. In the case of the blood collection tip 110, it is convenient to collect blood because peripheral blood can be collected rather than venous blood owing to the capillary phenomenon, and tuberculosis can be diagnosed with even a small amount of blood because the blood collection volume is determined from 30 to 100 μl depending on the length and area of the blood collection tip 110.

The dispensing nozzle 150 is attached to the second surface 148 of the support part 140, and a first tube fixing part 142 is attached to the side of the support part 140 to fix the tube that is coupled to the first surface 146. The second tube fixing part 144 is attached to the side of the support part 140 to fix the tube that is coupled to the second surface 148. The first tube fixing part 142 and the second tube fixing part 144 may be fitted using an elastic object such as a rubber ring, a teflon tape, etc. or may be screwed using thread.

Figure 3:
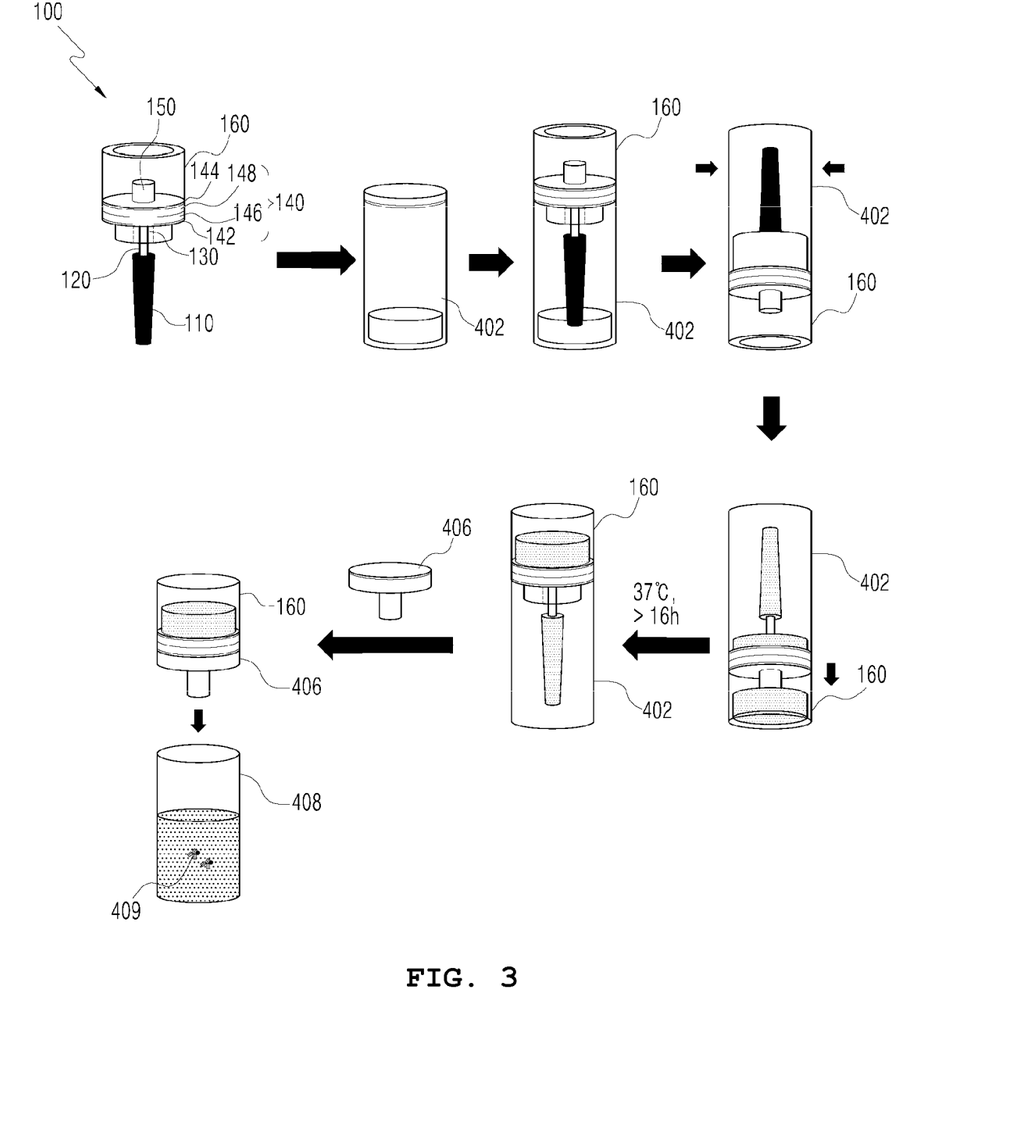
FIG. 3 illustrates a flow of diagnosis method and main configuration of a tuberculosis diagnosis apparatus according to an embodiment of the present invention.

FIG. 3 illustrates a flow of diagnosis method and main configuration of a tuberculosis diagnosis apparatus according to an embodiment of the present invention. Referring to FIG. 3, the tuberculosis diagnosis apparatus may include a dilution tube 402, a reaction tube 160, and a dispensing nozzle 150. The dilution tube 402 may be coupled to the first surface 146 to dilute the collected blood in the blood collection tip 110. The reaction tube 160 has antigens specific to *Mycobacterium tuberculosis* inside the container and is bound to the second surface 148, and can receive the solution 402 of the dilution tube to react it with the antigens. The dispensing nozzle 150 may be coupled to the second surface 148.

The tuberculosis diagnosis apparatus may further include a discharge nozzle 406 besides the blood collection device 100, the dilution tube 402, the reaction tube 160, and the dispensing nozzle 150.

The dilution tube 402 is coupled to the first tube fixing part 142 and is used to dilute the blood collected in the blood collection tip 110. The dilution tube 402 is preferably made of a material having elasticity so that the internal solution can move through the communication hole 130 of the support part 140 when external pressure is applied. The reaction tube 160 has antigens specific to *Mycobacterium tuberculosis* inside the container, and is coupled to the second tube fixing part 144. The reaction tube 160 receives the solution of the dilution tube 402 and reacts it with the antigens. The antigens specific to *Mycobacterium tuberculosis* may exist in a dried state in the reaction tube 160, and any formulation is possible if they are dried.

They can be dried by a hot air drying method, a constant temperature drying method, and a freeze drying method. In this case, the antigens specific to *Mycobacterium tuberculosis* may exist in a dried state along with substances such as antibodies, peptides, and nucleotides, if necessary, besides a stabilizer. The discharge nozzle 406 is fastened to the first surface 146 of the support part 140 and dispenses the solution in the reaction tube 160 coupled to the second tube fixing part 144.

The tuberculosis diagnosis apparatus may further include a buffer tube 408 that has a buffer and antibody conjugates specific for interferon gamma. The antibody conjugates specific for interferon gamma may exist in the buffer tube 408 in the form of granules 409 together with antibody conjugates specific for chicken immunoglobulin Y. And buffer may be added into the buffer tube 408 containing the granules 409 in order to dilute the granules 409. Each of the conjugates can be labeled with fluorescence. Later, antibody conjugates specific for interferon gamma and antibody conjugates specific for chicken immunoglobulin Y are used as an experimental group and as a control group respectively for tuberculosis diagnosis in the interferon gamma measurement cartridge 300.

Figure 4:
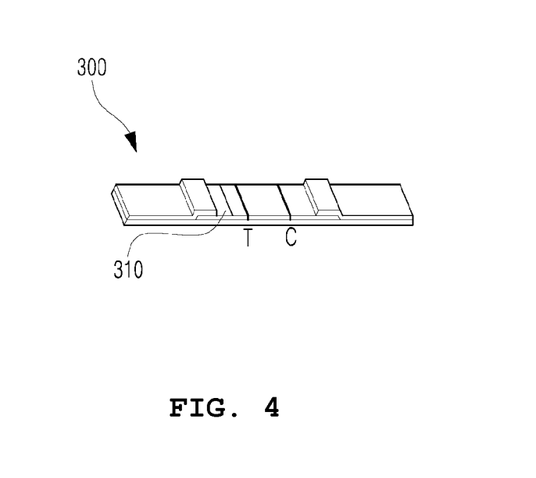
FIG. 4 depicts a configuration of an interferon gamma measurement cartridge according to an embodiment of the present invention.

FIG. 4 depicts a configuration of an interferon gamma measurement cartridge used in a tuberculosis diagnosis apparatus shown in FIG. 3 according to an embodiment of the present invention. Referring to FIGS. 3 and 4, the tuberculosis diagnosis apparatus may further include an interferon gamma measurement cartridge 300, and the interferon gamma measurement cartridge 300 may include a blood cell separation pad 310. After the blood collected in the blood collection tip 110 is diluted in the dilution tube 402, it moves to the reaction tube 160 through the communication hole 130 in the blood collection device 100 to meet the antigens specific to *Mycobacterium tuberculosis*. Then, the immune cells in the diluted blood react to the antigens specific to *Mycobacterium tuberculosis*. In the case that the immune cells in the blood have previously been exposed to *Mycobacterium tuberculosis*, when they encounter the *Mycobacterium tuberculosis* antigens again, CD T cells are more activated by memory T cells than when initially exposed to *Mycobacterium tuberculosis*, so interferon gamma is released much more. Eventually, if the solution in which was subjected to an immune response in the reaction tube 160 is mixed with the buffer and the antibody conjugates specific for interferon gamma in the buffer tube 408, the interferon gamma released by the immune response binds to the antibody conjugates specific for interferon gamma. And, for interferon gamma measurement, a certain amount of the mixed solution is dropped onto the blood cell separation pad 310 of the cartridge 300 through the discharge nozzle 406 that is fastened to the first surface 146 of the support part 140 and coupled to the first tube fixing part 142. The discharge nozzle 406 may be screwed and fastened to the first surface 146 of the support part 140.

The combination of the interferon gamma and the antibody conjugates specific for interferon gamma, and the antibody conjugates specific to chicken immunoglobulin Y pass through the blood cell separation pad 310 because they are smaller than the hole size of the blood cell separation pad 310, while other blood cells in the blood are filtered out by the blood cell separation pad 310 because they are larger than the hole size of the blood cell separation pad 310. Therefore, it is possible to prevent a non-specific reaction in which a blood cell present in the blood gets bound to an antibody specific for interferon gamma and chicken immunoglobulin Y, which are bound on the T and C positions on the cartridge 300, respectively. That is, tuberculosis can be more easily diagnosed using whole blood without a centrifugation process to separate blood cells from a blood sample.

Figure 5:
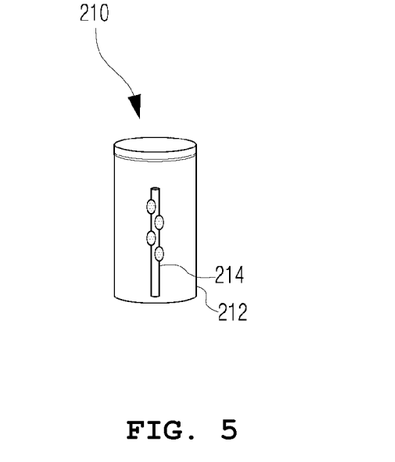
FIG. 5 is an exemplary view showing a wick to which antigens specific to *Mycobacterium tuberculosis* are immobilized according to another embodiment of the present invention.
Figure 6:
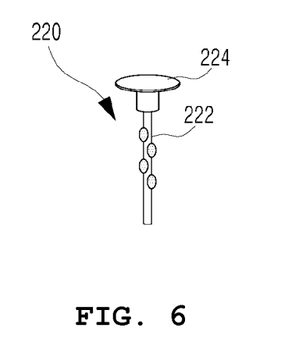
FIG. 6 is an exemplary view showing another wick to which antigens specific to *Mycobacterium tuberculosis* are immobilized according to another embodiment of the present invention.

FIG. 5 is an exemplary view showing a wick to which antigens specific to *Mycobacterium tuberculosis* are immobilized according to another embodiment of the present invention. In this case, it shows a reaction tube set 210 consisting of a combination of a reaction tube 212 and a wick 214 to which antigens specific to *Mycobacterium tuberculosis* are immobilized. FIG. 6 is an exemplary view showing another wick to which antigens specific to *Mycobacterium tuberculosis* are immobilized according to another embodiment of the present invention. It shows a combination 220 of a wick and stopper, consisting of a wick 222 to which antigens specific to *Mycobacterium tuberculosis* are immobilized and a stopper 224 coupled thereto.

Figure 7:
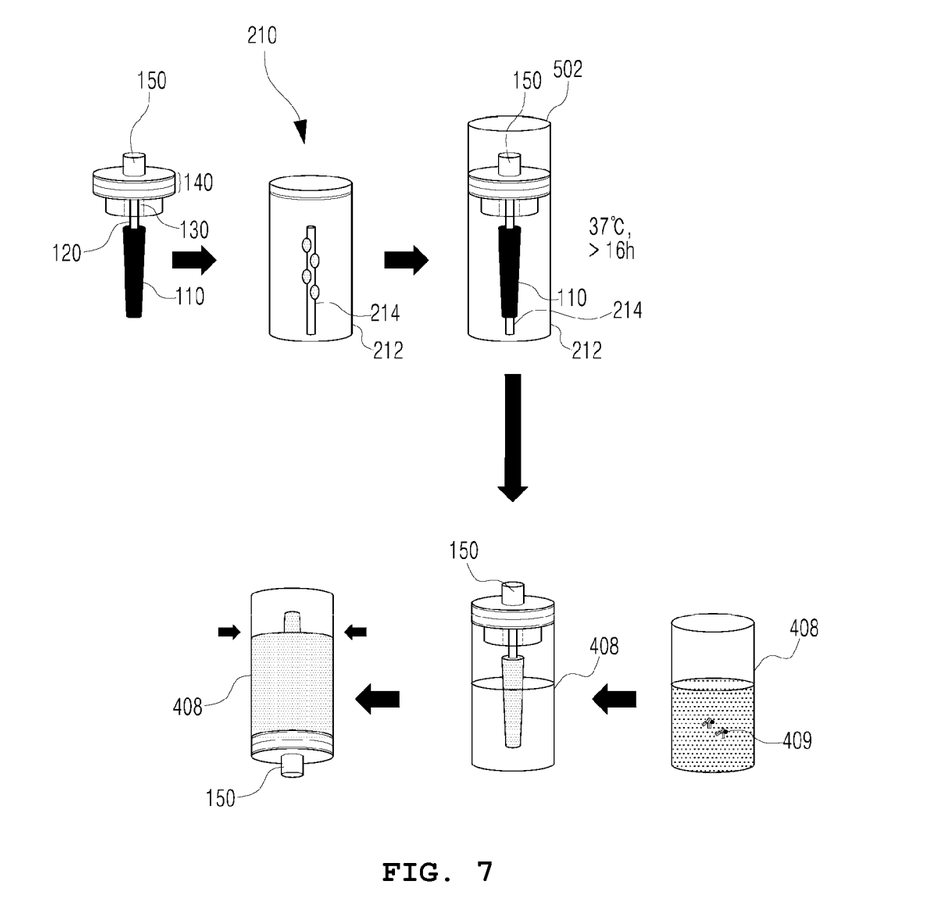
FIG. 7 illustrates a flow of diagnosis method and main configuration of a tuberculosis diagnosis apparatus in the case of using the wick to which antigens specific to *Mycobacterium tuberculosis* are immobilized as shown in FIG. 5.
Figure 8:
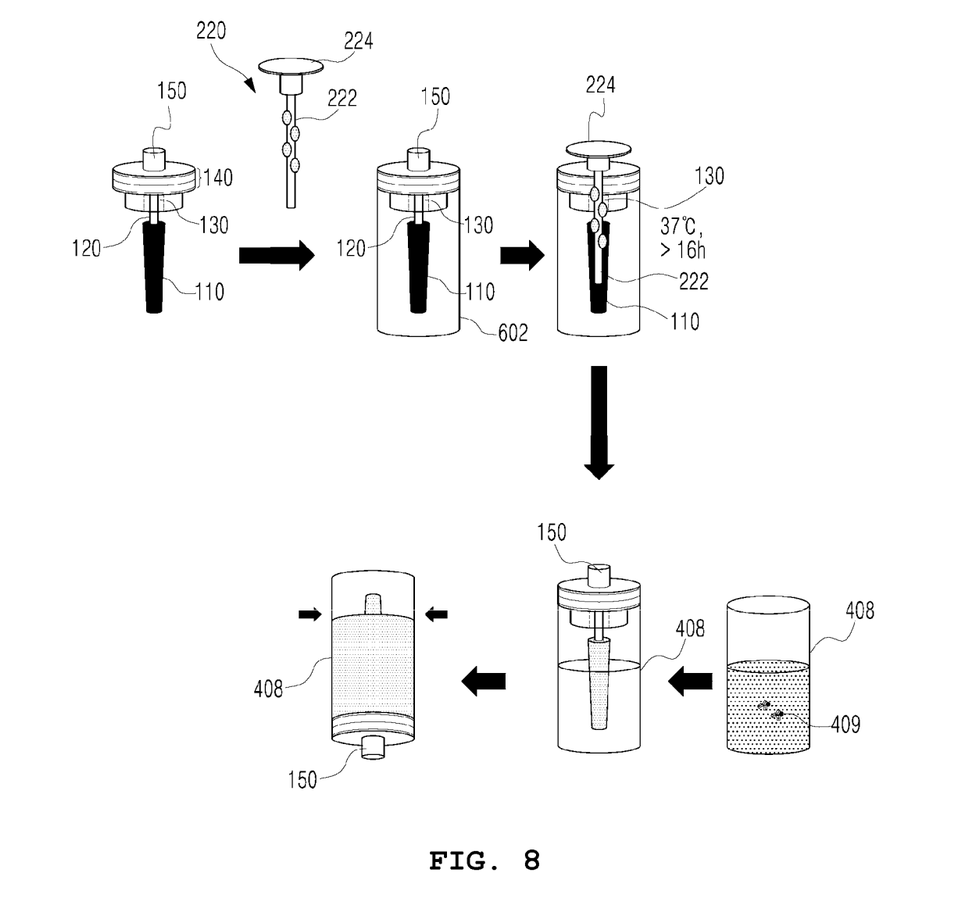
FIG. 8 illustrates a flow of diagnosis method and main configuration of a tuberculosis diagnosis apparatus in the case of using the wick to which antigens specific to *Mycobacterium tuberculosis* are immobilized as shown in FIG. 6.

FIG. 7 illustrates a flow of diagnosis method and main configuration of a tuberculosis diagnosis apparatus in the case of using the wick to which antigens specific to *Mycobacterium tuberculosis* are immobilized as shown in FIG. 5. FIG. 8 illustrates a flow of diagnosis method and main configuration of a tuberculosis diagnosis apparatus in the case of using the wick to which antigens specific to *Mycobacterium tuberculosis* are immobilized as shown in FIG. 6.

Referring to FIGS. 1-2A, 2B, and 5-8, the tuberculosis diagnosis apparatus according to another embodiment of the present invention may include a wick 214 and 222 in which antigens specific to *Mycobacterium tuberculosis* are immobilized, a reaction tube 212 and 602, and a buffer tube 408 besides a blood collection device 100. The reaction tube 212 and 602 is coupled to the first surface 146 and surrounds the blood collection tip 110. The buffer tube 408 is coupled to the first surface 146 and may be mixed with the residual blood in the blood collection tip 110, which was subjected to an immune response. The wick 214 and 222 has an outer diameter smaller than the inner diameter of the tip end of the blood collection tip, and antigens specific to *Mycobacterium tuberculosis* may be immobilized on the outer surface of the wick. The wick 214 and 222 may be rod-shaped wick, and the antigens specific for *Mycobacterium tuberculosis* may be in a dried state.

In more detail, antigens specific to *Mycobacterium tuberculosis* may be applied to the rod-shaped wick 214 and 222 in a dried state. There are two methods of application: a method of spraying antigen solution and a method of soaking the wick in the solution. It may be dried by a hot air drying method, a constant temperature drying method, and a freeze drying method. Besides stabilizer and antigens specific to *Mycobacterium tuberculosis*, substances such as antibodies, peptides, and nucleotides may be also applied together to the wick if necessary.

Referring to FIG. 5, a rod-shaped wick 214 to which antigens specific to *Mycobacterium tuberculosis* are attached may be vertically erected and coupled at the center of the bottom of the reaction tube 212. In this case, the first tube fixing part 142 may be provided with a cylindrical guide in order to allow the rod-shaped wick 214 to be easily coupled to the inside of the blood collection tip 110. And, a cap 502 may be coupled to the second tube fixing part 144 in order to prevent the loss caused by drying of blood during the immune response time.

Referring to FIG. 6, another rod-shaped wick 222 to which antigens specific to *Mycobacterium tuberculosis* are attached may exist separately without being coupled to the reaction tube 602. In this case, another rod-shaped wick 222 to which antigens specific to *Mycobacterium tuberculosis* are attached may pass the communication hole 130 through the hole of the dispensing nozzle 150 attached to the second surface 148 of the support part 140 so to be coupled to the inside of the blood collection tip 110. The reaction tube 602 has surrounds the combination of the wick and the blood collection tip. The buffer tube 408 is capable of being coupled to the first tube fixing part 142, and includes a buffer that can be mixed with the residual blood in the blood collection tip 110, which was subjected to an immune response, and antibody conjugates specific for interferon gamma. The antibody conjugates specific for interferon gamma may exist as granules 409 together with antibody conjugates specific for chicken immunoglobulin Y in the buffer tube 408. Each of the conjugates can be labeled with fluorescence. Later, antibody conjugates specific for interferon gamma and antibody conjugates specific for chicken immunoglobulin Y are used as an experimental group and as a control group respectively for tuberculosis diagnosis in the interferon gamma measurement cartridge. It is preferable that the buffer tube 408 is made of a material having elasticity so that the internal solution may move through the communication hole 130 of the support part 140 when external pressure is applied.

The mixed solution of the blood which was subjected to immune response, the buffer, and the granules 409 in the buffer tube 408 can be dispensed either through the dispensing nozzle 150 of the blood collection device 100, or through a separate discharge nozzle coupled to the second surface 148 of the support part 140. The discharge nozzle may be screwed and fastened to the second surface 144 of the support part 140.

The interferon gamma measurement cartridge shown in FIG. 4 may also be used for the tuberculosis diagnosis apparatus shown in FIGS. 7 and 8. Referring to FIGS. 7, 8 and 4, the tuberculosis diagnosis apparatus having the wick may further include an interferon gamma measurement cartridge 300, and the interferon gamma measurement cartridge 300 may include a blood cell separation pad 310. As described above, coupling the blood cell separation pad 310 to the cartridge 300 can prevent non-specific reactions in which the blood cells present in the blood from getting bound to an antibody specific for interferon gamma and chicken immunoglobulin Y, which are bound on the T and C positions on the cartridge 300, respectively. That is, tuberculosis can be more easily diagnosed using whole blood without a centrifugation process to separate blood cells from a blood sample.

Tuberculosis diagnosis method according to an embodiment of the present invention comprises the steps of: diluting the blood collected by the blood collection tip 110 of the blood collection device 100; reacting the diluted solution with antigens specific to *Mycobacterium tuberculosis* in the reaction tube 160; and dispensing the solution of the reaction tube 160.

Referring to FIGS. 1 to 3, after the dilution tube 402 is coupled to the first tube fixing part 142, the blood collected by the blood collection tip 110 is diluted with the dilution tube 402. It is preferable that the dilution tube 402 is made of a material having elasticity so that the internal solution may move through the communication hole 130 of the support part 140 when external pressure is applied.

After coupling the reaction tube 160 having antigens specific to *Mycobacterium tuberculosis* inside to the second tube fixing part 144, the solution of the dilution tube 402 is transferred to the reaction tube 160. The antigens specific to *Mycobacterium tuberculosis* may exist in a dried state in the reaction tube 160, and any formulation is possible if they are dried. They can be dried by a hot air drying method, a constant temperature drying method, and a freeze drying method. The antigens specific to *Mycobacterium tuberculosis* may exist in a dried state along with substances such as antibodies, peptides, and nucleotides, if necessary, besides a stabilizer.

After reacting the dilution transferred to the reaction tube 160 with antigens specific to *Mycobacterium tuberculosis* present in the reaction tube 160, the dilution tube 402 and the blood collection tip 110 are removed. After that, the discharge nozzle 406 is mounted on the first surface 146 of the support part 140 and the solution of the reaction tube 160 is dispensed through it. The solution in the reaction tube 160 may be dispensed into the buffer tube 408 containing a buffer and antibody conjugates specific for interferon gamma through the discharge nozzle 406. The discharge nozzle 406 may be screwed and fastened to the first surface 146 of the support part 140.

The antibody conjugates specific for interferon gamma may exist in the buffer tube 408 in the form of granules 409 together with antibody conjugates specific for chicken immunoglobulin Y. Each of the conjugates can be labeled with fluorescence. Later, antibody conjugates specific for interferon gamma and antibody conjugates specific for chicken immunoglobulin Y are used as an experimental group and as a control group respectively for tuberculosis diagnosis in the interferon gamma measurement cartridge 300.

Referring to FIG. 4, the tuberculosis diagnosis method may comprise the step of dispensing the solution of the reaction tube 160 into the buffer tube 408 and dropping the solution of the buffer tube 160 into the interferon gamma measurement cartridge 300. The interferon gamma measurement cartridge 300 may further include a blood cell separation pad 310. As described above, the blood cell separation pad 310 is coupled to the cartridge 300 so that it is possible to prevent a non-specific reaction in which a blood cell present in the blood gets bound to an antibody specific for interferon gamma and chicken immunoglobulin Y, which are bound on the T and C positions on the cartridge 300, respectively. That is, tuberculosis can be more easily diagnosed using whole blood without a centrifugation process to separate blood cells from a blood sample.

In another embodiment of the present invention, a tuberculosis diagnosis method comprises the steps of: inserting a wick 214 and 222 to which antigens specific to *Mycobacterium tuberculosis* are immobilized into a blood collection tip 110 of a blood collection device 100; reacting the antigens specific to *Mycobacterium tuberculosis* with blood in the blood collection tip 110; contacting the reacted blood in the blood collection tip 110 with the inside of a buffer tube 408 containing a buffer and antibody conjugates specific for interferon gamma; and dispensing a solution of a buffer tube 408, wherein the solution was contacted with the reacted blood in the blood collection tip 408.

Referring to FIGS. 1, 2A, 2B, 5 to 8, the reaction tube 212 and 602 is coupled to the first tube fixing part 142, and a wick 214 and 222 is inserted into a blood collection tip 110, so as to react the blood in the blood collection tip 110 with the antigens specific to *Mycobacterium tuberculosis* immobilized on the outer surface of the wick 214. The antigens specific for *Mycobacterium tuberculosis* may be in a dried state. In more detail, antigens specific to *Mycobacterium tuberculosis* may be applied to the rod-shaped wick 214 and 222 in a dried state. There are two methods of application: a method of spraying antigen solution and a method of soaking the wick in the solution. It may be dried by a hot air drying method, a constant temperature drying method, and a freeze drying method. Besides stabilizer and antigens specific to *Mycobacterium tuberculosis*, substances such as antibodies, peptides, and nucleotides may be also applied together to the wick 214 and 222 if necessary.

The wick 214 to which antigens specific to *Mycobacterium tuberculosis* are immobilized may be vertically erected and coupled at the center of the bottom of the reaction tube 212. In this case, the first tube fixing part 142 may be provided with a cylindrical guide in order to allow the wick 214 to be easily coupled to the inside of the blood collection tip 110. And, a cap 502 may be coupled to the second tube fixing part 144 in order to prevent the loss caused by drying of blood during the immune response time.

The wick 222 to which antigens specific to *Mycobacterium tuberculosis* are immobilized may exist separately without being coupled to the reaction tube 602. The wick 222 to which antigens specific to *Mycobacterium tuberculosis* are immobilized may pass the communication hole 130 through the hole of the dispensing nozzle 150 attached to the second surface 148 of the support part 140 so to be coupled to the inside of the blood collection tip 110.

The reaction tube 212 and 602 is removed from the first tube fixing part 142, and is coupled to the buffer tube 408 containing a buffer and antibody conjugates specific for interferon gamma. And then, the buffer tube 408 is shaken so as to make the antibody conjugates specific for interferon gamma to contact the blood in the blood collection tip 110, which reacted to the antigens specific to *Mycobacterium tuberculosis*. It is preferable that the buffer tube 408 is made of a material having elasticity so that the internal solution may move through the communication hole 130 of the support part 140 when external pressure is applied. The antibody conjugates specific for interferon gamma may exist in the buffer tube 408 in the form of granules 409 together with antibody conjugates specific for chicken immunoglobulin Y. The antibody conjugates specific for interferon gamma and the antibody conjugates specific for chicken immunoglobulin Y can be labeled with fluorescence and exist in the buffer tube 408 in the form of granules 409. When the granules 409 are diluted with the buffer, the buffer tube 408 is shaken so as to make the antibody conjugates specific for interferon gamma to contact the blood in the blood collection tip 110, which reacted to the antigens specific to *Mycobacterium tuberculosis*. Later, antibody conjugates specific for interferon gamma and antibody conjugates specific for chicken immunoglobulin Y are used as an experimental group and as a control group respectively for tuberculosis diagnosis in the interferon gamma measurement cartridge 300.

The mixed solution of the residual blood in the blood collection tip 110, which was subjected to immune response, the buffer, and the granules 409 in the buffer tube 408 can be dispensed through the dispensing nozzle 150 of the blood collection device 100. And also it can be dispensed through a separate discharge nozzle coupled to the second surface 148 of the support part 140. The discharge nozzle may be screwed and fastened to the second surface 144 of the support part 140.

Referring to FIG. 4, the dispensed solution of the buffer tube 408 may be dropped onto the interferon gamma measurement cartridge 300 afterwards, and the interferon gamma measurement cartridge 300 may include a blood cell separation pad 310. As described above, it is possible to prevent a non-specific reaction in which a blood cell present in the blood gets bound to an antibody specific for interferon gamma and chicken immunoglobulin Y, which are bound on the T and C positions on the cartridge 300, respectively. That is, tuberculosis can be more easily diagnosed using whole blood without a centrifugation process to separate blood cells from a blood sample.

Hereinafter, the present invention will be described in more detail through examples. These examples are for illustrative purposes only and it is obvious to those skilled in the art that the scope of the present invention is not limited thereto.

Embodiment 1

Referring to FIGS. 1 to 4, after releasing blood on a finger or a peripheral part by using a device such as a lancet, the blood collection tip 110 is brought to the released blood so that the blood may fill up in the blood collection tip 110 by the capillary phenomenon. When the blood collection tip 110 is filled with 30 to 100 μL of blood, the dilution tube 402 is coupled to the first tube fixing part 142, and then the coupled device is shaken to mix the blood and the dilution buffer. Then, the coupled device is turned over so that the diluted blood solution may be moved to the reaction tube 160 coupled to the second tube fixing part 144 through the communication hole 130 of the support part 140. And, the blood solution and the antigens specific to *Mycobacterium tuberculosis* in the reaction tube 160 are brought into contact. After that, it reacts them in an incubator at 37° C. for more than 16 hours so as to trigger an immune response between immune cells in the blood and the antigens specific to *Mycobacterium tuberculosis*. After the above-mentioned time has elapsed, the dilution tube 402 is removed from the first tube fixing part 142, and then a discharge nozzle 190 for dispensing the solution of the reaction tube 160 is coupled to the first surface 142 of the support part 140. And next, the side of the reaction tube 160 is pressed, and a certain amount of the reaction solution in the reaction tube 160 is transferred to a buffer tube 408 in which a buffer and antibody conjugates specific for interferon gamma are mixed, so that they may get sufficiently mixed.

Thereafter, a certain amount of the mixed solution is transferred and dropped onto the blood cell separation pad 310 disposed on the interferon gamma measurement cartridge 300. The blood cells in the blood are filtered out by the blood cell separation pad 310 while the combination of the interferon gamma and the antibody conjugates specific for interferon gamma, and the antibody conjugates specific to chicken immunoglobulin Y pass through the blood cell separation pad 310 so that each of them may reach T and C positions which are detection parts of the cartridge 300. The combination of the antibody conjugates specific for interferon gamma and the interferon gamma that passed through the blood cell separation pad 310 binds to an antibody specific for interferon gamma at the T position while the antibody conjugate specific for the chicken immunoglobulin Y binds to the chicken immunoglobulin Y at the C position. 15 minutes later, the brightness of the fluorescence at the T and C positions was measured and compared so as to confirm the expression degree of interferon gamma expressed by *Mycobacterium tuberculosis*.

Embodiment 2

Referring to FIGS. 1, 2A, 2B, and 4 to 8, after releasing blood on a finger or a peripheral part by using a device such as a lancet, the blood collection tip 110 is brought to the released blood so that the blood may fill up in the blood collection tip 110 by the capillary phenomenon. When the blood collection tip 110 is filled with 30 to 100 μL of blood, the cylindrical guide coupled to the first tube fixing part 142 and the reaction tube 212 are engaged with each other. The rod-shaped wick 214 which is vertically coupled to the center of the bottom of the reaction tube 212, is inserted into the inside of the tip of the blood collection tip 110. At this time, the reaction tube 212 is coupled to the first tube fixing part. Then, the cap 502 is coupled to the second tube fixing part 144 in order to prevent the loss caused by drying of the blood during the following reaction time.

Another rod-shaped wick 222 to which antigens specific to *Mycobacterium tuberculosis* are attached may pass the communication hole 130 through the hole of the dispensing nozzle 150 attached to the second surface 148 of the support part 140 so to be coupled to the inside of the blood collection tip 110. At this time, the reaction tube 602 is coupled to the first tube fixing part 142 without a circular guide.

Afterwards, the antigens specific to *Mycobacterium tuberculosis* attached to the outer surface of the rod-shaped wick 214 and 222 and the blood in the blood collection tip 110 are reacted in an incubator at 37° C. for more than 16 hours so as to trigger an immune response between the immune cells in the blood and the antigens specific to *Mycobacterium tuberculosis*. After the above time has elapsed, the cap 502 coupled to the reaction tube 212 and 602 and the second tube fixing part 144 are removed from them, and the buffer tube 408 containing buffer and antibody conjugates specific for interferon gamma is coupled to the tube fixing part 142. And then, the buffer tube 408 is shaken so that the blood in the blood collection tip 110, which reacted to the antigens specific to *Mycobacterium tuberculosis*, may contact the antibody conjugates specific for interferon gamma. Afterwards, the solution in the buffer tube 408 can be dispensed either through the dispensing nozzle 150 of the blood collection device 100 or through a separate discharge nozzle coupled to the second surface 148 of the support part 140 so that it may be dropped onto the blood cell separation pad 310 disposed on the interferon gamma measurement cartridge 300. The blood cells in the blood are filtered out by the blood cell separation pad 310 while the combination of the interferon gamma and the antibody conjugates specific for interferon gamma, and the antibody conjugates specific to chicken immunoglobulin Y pass through the blood cell separation pad 310 so that each of them may reach T and C positions which are detection parts of the cartridge 300. The combination of the antibody conjugates specific for interferon gamma and the interferon gamma that passed through the blood cell separation pad 310 binds to an antibody specific for interferon gamma at the T position while the antibody conjugate specific for the chicken immunoglobulin Y binds to the chicken immunoglobulin Y at the C position. 15 minutes later, the brightness of the fluorescence at the T and C positions was measured and compared so as to confirm the expression degree of interferon gamma expressed by *Mycobacterium tuberculosis*.

The invention claimed is:

1. A tuberculosis diagnosis apparatus comprising:
 a support part including a first side, a second side formed opposite the first side and having a dispensing nozzle, and a communication hole through which a solution can move between the first side and the second side;
 a blood collection tip attached to the first side and having a capillary formed therein;
 a rod-shaped part having an outer diameter smaller than an inner diameter of the blood collection tip, which is inserted into the capillary of the blood collection tip, and to which an antigen specific to *Mycobacterium tuberculosis* is immobilized; and
 a reaction tube coupled to the first side and surrounding the blood collection tip, wherein an immune response takes place.

2. The tuberculosis diagnosis apparatus of claim 1, wherein the antigen specific to *Mycobacterium tuberculosis* is in a dried state.

3. The tuberculosis diagnosis apparatus of claim 1, further comprising a buffer tube coupled to the first side and filled with antibody conjugates specific for interferon gamma and buffer.

4. The tuberculosis diagnosis apparatus of claim 3, further comprising an interferon gamma measurement cartridge.

5. The tuberculosis diagnosis apparatus of claim 4, wherein the interferon gamma measurement cartridge includes a blood cell separation pad.

* * * * *